United States Patent

George et al.

[11] Patent Number: 5,244,901
[45] Date of Patent: Sep. 14, 1993

[54] 4-PYRIMIDINECARBOXAMIDE DERIVATIVES, THEIR PREPARATION AND THEIR APPLICATION IN THERAPY

[75] Inventors: Pascal George, St. Arnoult en Yvelines; Jacques Froissant, Moree; Arlette Tixidre, Orsay, all of France

[73] Assignee: Synthelabo, Paris, France

[21] Appl. No.: 903,705

[22] Filed: Jun. 26, 1992

[30] Foreign Application Priority Data

Jun. 27, 1991 [FR] France ................................ 91 07937

[51] Int. Cl.$^5$ ................ C07D 401/12; A61K 31/505
[52] U.S. Cl. ..................................... 514/252; 544/295
[58] Field of Search ....................... 544/295; 514/252

[56] References Cited

U.S. PATENT DOCUMENTS

| | | | |
|---|---|---|---|
| 4,853,387 | 8/1989 | Manoury et al. | 514/272 |
| 4,891,376 | 1/1990 | Manoury et al. | 514/272 |
| 4,929,621 | 5/1990 | Manoury et al. | 514/275 |

FOREIGN PATENT DOCUMENTS

| | | |
|---|---|---|
| 0435749 | 7/1991 | European Pat. Off. |
| 2143730 | 3/1973 | Fed. Rep. of Germany |

Primary Examiner—John M. Ford
Attorney, Agent, or Firm—Jacobson, Price, Holman & Stern

[57] ABSTRACT

The present invention provides a compound which is a 4-pyrimidinecarboxamide derivative of general formula (I)

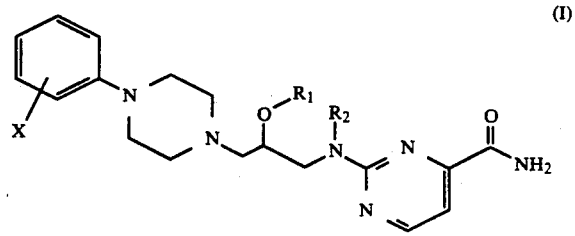

in which
X represents one or more substituents independently chosen from fluorine, chlorine, methoxy and cyclopropyl,
$R_1$ represents a hydrogen atom or a $C_1$–$C_3$ alkyl group, and
$R_2$ represents a hydrogen atom or a methyl group, or a pharmaceutically acceptable acid addition salt thereof; their preparation and their application in therapy.

14 Claims, No Drawings

4-PYRIMIDINECARBOXAMIDE DERIVATIVES, THEIR PREPARATION AND THEIR APPLICATION IN THERAPY

The present invention relates to 4-pyrimidinecarboxamide derivatives, to their preparation and to their application in therapy.

SUMMARY OF THE INVENTION

The present invention provides a compound which is a 4-pyrimidinecarboxamide derivative of general formula (I)

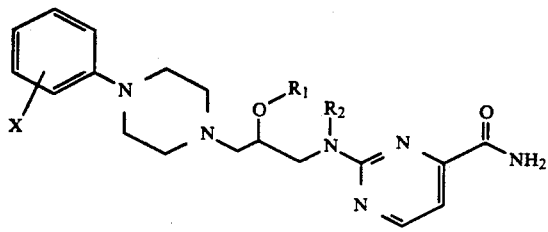

in which
X represents one or more substituents independently chosen from fluorine, chlorine, methoxy and cyclopropyl,
$R_1$ represents a hydrogen atom or a $C_1$-$C_3$ alkyl group, and
$R_2$ represents a hydrogen atom or a methyl group, or a pharmaceutically acceptable acid addition salt thereof.

The present invention also relates to a process for the preparation of the 4-pyrimidinecarboxamide derivatives and their salts and to their therapeutic use.

The compounds of the invention exist in the form of pure enantiomer or mixture of enantiomers, for example a racemic mixture, in the state of free bases or of addition salts with pharmaceutically acceptable acids.

DETAILED DESCRIPTION OF THE INVENTION

According to a preferred embodiment, X represents one or two substituents independently chosen from fluorine, chlorine, methoxy and cyclopropyl and $R_1$ represents hydrogen methyl or n-propyl. Preferably, the pharmacetically acceptable acid addition salt is the hydrochloride, acid fumarate or neutral fumarate.

Examples of specific compounds of the invention include:

(±)-2-[{3-[4-(5-chloro-2-phenoxyphenyl)-1-piperazinyl]-2hydroxypropyl}amino]-4-pyrimidinecarboxamide or the hydrochloride thereof;

(±)-2-[{3-[4-(5-chloro-2-methoxyphenyl)-1-piperazinyl]-2hydroxypropyl}methylamino]-4-pyrimidinecarboxamide or the hydrochloride thereof;

(+)-2-[{3-[4-(5-fluoro-2-methoxyphenyl)-1-piperazinyl]-2hydroxypropyl}amino]-4-pyrimidinecarboxamide or the fumarate thereof;

(−)-2-[{3-[4-(5-fluoro-2-methoxyphenyl)-1-piperazinyl]-2hydroxypropyl}amino]-4-pyrimidinecarboxamide or the fumarate thereof; and (±)-2-[(3-[4-(5-chloro-2-methoxyphenyl)-1-piperazinyl]-2methoxypropyl}amino]-4-pyrimidinecarboxamide.

The compounds of the general formula (I) may be prepared according to the process in Scheme 1 below.

A piperazine of general formula (II), in which X is as defined above, is reacted with an epoxide reactant of formula (III), in which Y represents a

Scheme 1

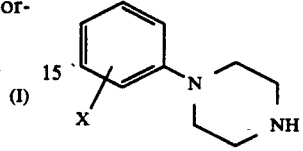

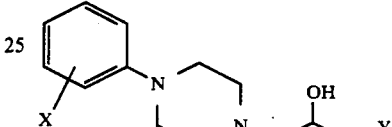

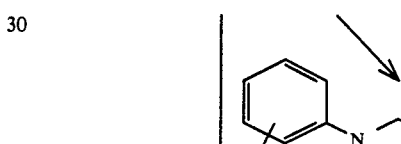

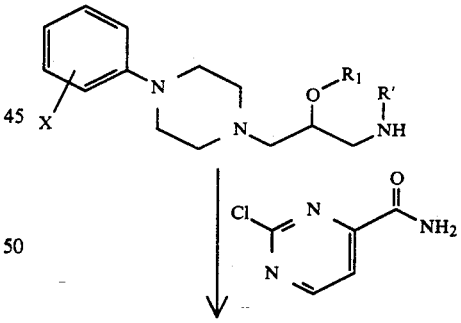

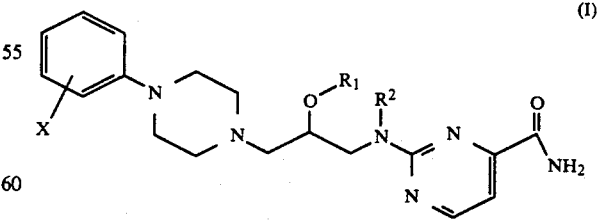

phthalimido group. The reaction is performed in a protic solvent such as an aliphatic alcohol, for example 2-propanol, typically at a temperature of 20° to 100° C.

A 1-amino-2-propanol derivative of general formula (IVa) is obtained, which derivative is treated with hydrazine hydrate in a protic solvent such as an aliphatic alcohol, for example ethanol, typically at a temperature of 20° to 80 C., and then with aqueous hydrochloric acid typically at a temperature of 80° to 100° C., to obtain the hydrochloride of the amine of general formula (V), according to the conventional conditions for conversion of a substituted phthalimide to an amine. The compound of general formula (V) in which R' represents hydrogen is then reacted with 2-chloro-4-pyrimidinecarboxamide of formula (VI), in an aprotic solvent, for example N,N-dimethylformamide, in the presence of a base for example potassium carbonate, typically at a temperature of 20° to 60° C., to obtain a compound of general formula (I) in which $R_1$ and $R_2$ are each a hydrogen atom.

The compounds of general formula (I) in which $R_2$ represents a methyl group are obtained by treating an amino alcohol of general formula (V) in which R' represents hydrogen with an alkyl formate, for example ethyl formate, typically at a temperature of 40° to 60° C. A formyl derivative of general formula (V) in which R' represents a formyl group is thereby obtained, which derivative is reduced in the presence of lithium aluminium hydride in an inert solvent of the ether type, such as tetrahydrofuran, typically at a temperature of 20° to 60° C.

The latter compound is then reacted with 2-chloro-4-pyrimidinecarboxamide of formula (VI) in the manner described above.

If it is desired to prepare a compound of general formula (I) in which $R_1$ represents a $C_1$–$C_3$ alkyl group, the compound of general formula (IVa) is converted to a compound of general formula (IVb), in which X is as defined above and Z represents an amine-protective group other than a phthalimido group, for example a triphenylmethyl group, first by deprotection of the compound of general formula (IVa) by means of hydrazine hydrate, and then by protection of the amine thereby liberated by means of triphenylmethyl chloride, under basic conditions, for example in the presence of triethylamine and in an aprotic solvent such as dichloromethane, typically at a temperature of 20° to 40° C. The compound of general formula (IVb) is then reacted with a $C_1$–$C_3$ alkyl halide, in the presence of a base such as sodium hydride, in an aprotic solvent such as tetrahydrofuran, at a temperature of 20° to 50° C. On deprotection of the amine function of the compound thereby obtained, for example by means of gaseous hydrochloric acid in a protic solvent such as methanol, typically at a temperature of 20° to 65° C., the compound of general formula (V) in which $R_1$ represents a $C_1$–$C_3$ alkyl group and R' represents a hydrogen atom is obtained which is then reacted with 2-chloro-4-pyrimidinecarboxamide in the manner described above.

If desired the compound of formula (I) may be converted into a pharmaceutically acceptable acid addition salt in a manner known per se.

A variant of the process according to Scheme 1 consists in using, instead of the epoxide of the formula (III), the alcohol of formula (III')

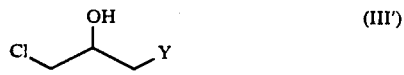

(III')

in which Y is as defined above. The reaction with the compound of general formula (II) is then performed in a solvent such as xylene at the refluxing temperature.

The starting epoxide of general formula (III) is commercially available.

2-Chloro-4-pyrimidinecarboxamide of formula (VI) may be prepared from 2-chloro-4-pyrimidinecarbonitrile by treatment with gaseous hydrochloric acid in formic acid, the said nitrile itself being prepared according to the method described in J. Het. Chem., 1964, 1, 130–133.

The starting compound of formula (III') may be obtained from the compound of formula (III) by opening the epoxide ring by means of hydrochloric acid.

If it is desired to obtain an optically pure compound of general formula (I), it is possible, for example, to employ a conventional method of fractional crystallisation of diastereoisomers after preparing an ester or a carbamate of the compound of general formula (I) (in which $R_1$ represents a hydrogen atom) by means of an optically pure acid.

It is also possible to employ the process in Scheme 1 with an optically pure compound of general formula (III') which has been isolated, for example, by an enzymatic method.

The basic principle of such a method consists in separating an optically pure alcohol and the corresponding acetate, having the opposite configuration, for example by chromatography on a silica gel column.

According to a first variant, the racemic compound of the formula (III') is subjected to a chemical acetylation, for example by means of acetic anhydride, only one of the two enantiomers of the racemic acetate thereby obtained is then hydrolysed in the presence of an enzyme, and the acetate which has not been hydrolysed is separated. An optically pure alcohol and an optically pure acetate of the opposite configuration are obtained, it being possible, if so desired, for the latter compound itself to be hydrolysed chemically to yield the second enantiomer of the alcohol.

According to a second variant, the racemic compound of formula (III') is subjected to a stereospecific acetylation in the presence of an enzyme which catalyses the esterification of only one of the enantiomers, for example by means of vinyl acetate. As above, an optically pure alcohol and an optically pure acetate of the opposite configuration are obtained, it being possible, if so desired, for the latter compound itself to be hydrolysed chemically to yield the second enantiomer of the alcohol.

In both variants, it is possible, depending on the enzyme used, to obtain the laevorotatary or dextrorotatary enantiomer of the compound of formula (III') and its acetate of the opposite configuration.

Enzymes which can be used are, for example, the enzymes 30 AY of Amano (trade mark) ("Lipase P"), Lipolase 100 of Novo Nordisk (trade mark), sheep pancreas acetone powder of Sigma (trade mark), rabbit liver esterase of Sigma (trade mark), Palatase A 750 of Novo Nordisk (trade mark), Lipase OF of Sepracor (trade mark), wheat germ Lipase Type I of Sigma (trade mark), Pig Liver Esterase of Biocatalysts (trade mark) and, preferably, Pig Liver Esterase of Sigma (trade mark), Lipoprotein Lipase of Amano (trade mark), porcine pancreas acetone powder of Sigma (trade mark) and porcine liver acetone powder of Sigma (trade mark).

The examples which follow illustrate the preparation of a few compounds according to the invention.

Elemental microanalyses and the IR and NMR spectra confirm the structures of the products obtained.

Example 1 (Compound No. 3)

(±)-2-[{3-[4-(5-Chloro-2-phenoxyphenyl)-1-piperazinyl]-2-hydroxypropyl}amino]-4-pyrimidinecarboxamide hydrochloride.

1.1.  (±)-2-{2-[4(5-Chloro-2-methoxyphenyl)-1-piperazinyl]-2-hydroxypropyl}-1H-isoindole-1,3(2H)-dione.

8.13 g (40 mmol) of N-(2,3-epoxypropy)phthalimide are added to a solution of 9.98 g (41.7 mmol) of 1-(5-chloro-2-methoxyphenyl)-piperazine in 150 ml of 2-propanol, and the mixture is heated to the refluxing temperature of the solvent for 3.5 hours and then left stirring overnight at room temperature. The precipitate is collected by filtration, washed with methanol and dried under reduced pressure. A solid is obtained which melts at 136°–138° C., which product is used in the next step without further purification.

1.2.  (±)-α-(Aminomethyl)-4-(5-chloro-2-methoxyphenyl)-1-piperazineethanol.

2.5 ml, equivalent to 2.58 g (48.4 mmol), of hydrazine hydrate are added to a solution of 300 ml of ethanol containing the compound 1.1., and the mixture is then heated to the refluxing temperature of the solvent for 3.5 hours. The solution is cooled, the solvent is evaporated off under reduced pressure, the residue is treated with 70 ml of water and 10 ml of 36% hydrochloric acid, and the reaction mixture is heated to 100° C. for 1 hour and then left at room temperature overnight. The water-insoluble phthalohydrazide is removed by filtration, the filtrate is cooled to 0° C., ethyl acetate is added to it and 30% sodium hydroxide is added until the pH is ≧8. After several extractions with ethyl acetate, the organic phases are combined and dried over sodium sulphate. The solvent is evaporated off under reduced pressure. 9.9 g of oil are obtained, which product is used in the next step without further purification.

1.3  (±)-2-[{3-[4-(5-Chloro-2-methoxyphenyl)-1-piperazinyl]-2-hydroxypropyl}amino]-4-pyrimidinecarboxamide hydrochloride.

1.6 g (10.15 mmol) of 2-chloro-4-pyrimidinecarboxamide and 2.4 g (17.36 mmol) of potassium carbonate are added to a solution of 4.75 g (15.84 mmol) of the compound 1.2. in 150 ml of acetonitrile. The mixture is stirred at room temperature for 24 hours and then heated to reflux for 3 hours. It is partially concentrated under reduced pressure, water is added and the reaction product is extracted with dichloromethane.

The organic phase is dried over sodium sulphate and concentrated under reduced pressure. An oil is obtained, which oil is purified by chromatography on a silica gel column (eluent: dichloromethane, then ethyl acetate, then ethyl acetate/methanol 98:2 to 85:15). 1.45 g of an oil are isolated, which product crystallises and which is recrystallised in acetonitrile.

Melting point: 141°–142° C.

The hydrochloride is prepared from 1.43 g (3.39 mmol) of base dissolved in 10 ml of dichloromethane and 34 ml of 0.1 N solution of hydrochloric acid in 2-propanol. The solution is concentrated under reduced pressure and the residue is recrystallised in acetone. 1.4 g of hydrochloride are obtained.

Melting point: 231°–235° C. (decomposition).

Example 2 (Compound No. 5)

(±)-2-[{3-[4-(5-Chloro-2-methoxyphenyl)-1-piperazinyl]-2-hydroxypropyl}methylamino]-4-pyrimidinecarboxamide hydrochloride.

2.1.  (±)-N-{3-[4-(5-Chloro-2-methoxyphenyl)-1-piperazinyl]-2-hydroxypropyl}formamide.

A solution of 5.15 g (17.01 mmol) of the compound 1.2. in 50 ml of ethyl formate is heated to the refluxing temperature for 5 hours, and the excess ethyl formate is then evaporated off under reduced pressure.

An oily residue is obtained, which residue is purified by chromatography on a silica gel column (eluent: ethyl acetate/methanol 99:1 then 90:10). 5.10 g of oil are isolated, which product is used in the next step without further purification.

2.2.  (±)-α-[(Methylamino)methyl]-4-(5-chloro-2-methoxyphenyl)-1-piperazineethanol.

0.9 g (23.7 mmol) of lithium aluminium hydride, 20 ml of dry tetrahydrofuran and, dropwise, a solution of 5.10 g (15.55 mmol) of compound 2.1. in 100 ml of dry tetrahydrofuran are introduced successively into a 0.5–1 round-bottomed flask. The mixture is heated to the refluxing temperature for 5 hours, then allowed to return to room temperature and hydrolysed with aqueous sodium hydroxide solution. The product is extracted by means of diethyl ether. The organic phases are combined, dried over sodium sulphate and concentrated. 4.54 g of oily residue are obtained, which product is used in the next step without further purification.

2.3.  (±)-2-[{3-[4-(5-Chloro-2-methoxyphenyl)-1-piperazinyl]-2-hydroxypropyl}methylamino]-4-pyrimidinecarboxamide hydrochloride.

4.5 g (14.33 mmol) of the compound 2.2., 2 g (12.6 mmol) of 2-chloro-4-pyrimidinecarboxamide, 2.4 g (17.36 mmol) of potassium carbonate and 200 ml of acetonitrile are introduced successively into a 0.5–1 round-bottomed flask, and the mixture is stirred for 32 hours at room temperature.

It is concentrated under reduced pressure, water is added to the residue and the mixture is extracted with dichloromethane. The organic phase is dried over sodium sulphate and the solvent is then evaporated under reduced pressure. The residue is purified by chromatography on a silica gel column (eluent: dichloromethane/methanol from 99:1 to 85:15). The evaporation residue is crystallised in acetonitrile and 1.48 g of solid are obtained.

Melting point: 135°–136° C.

The hydrochloride is prepared from 1.48 g (3,4 mmol) of base dissolved in 10 ml of dichloromethane and 1 ml of methanol, and 34 ml of 0.1 N hydrochloric acid in 2-propanol. The solution is concentrated and the residue is crystallised in acetone. 1.32 g of white solid are obtained.

Melting point: 231°–235° C. (decomposition).

Example 3 (Compound No. 2b)

(+)-2-[(3-[4-(5-Fluoro-2-methoxyphenyl)-1-piperazinyl]-2-hydroxypropyl}amino]-4-pyrimidinecarboxamide fumarate.

3.1.  (-)-2-(3-Chloro-2-hydroxypropyl)-1H-isoindole-1,3(2H)-dione.

4 g (0.009 mol) of 1-chloro-3-(1,3-dioxo-1H(2H)-isoindol-2-yl)-2-propyl acetate are dissolved in 50 ml of tert-butyl methyl ether, 200 ml of phosphate buffer (potassium dihydrogen phosphate and dipotassium hydrogen phosphate, 0.01 M, pH 7.2) and then 0.4 g of porcine liver acetone powder are added, and the mixture is stirred at room temperature for 18 hours while the pH is maintained at 7.2 by adding 1 N sodium hydroxide using a pH-stat.

The mixture is filtered, the organic phase is separated and washed with saturated sodium chloride solution and dried over sodium sulphate, and the solvent is evaporated off at reduced pressure. The residue is purified by chromatography on a silica gel column, eluting with a cyclohexane/ethyl acetate 70:30 mixture.

1.5 g of alcohol rich in dextrorotatory enantiomer and 1.64 g of pure laevorotatory acetate are obtained.

Melting point of the acetate: 88°-90° C.
Optical rotation: $[\alpha]_D^{20} = 17.8°$ (c=0.78; EtOH).
Enantiomeric excess: ee=90%.

The acetate is subjected to a chemical hydrolysis by means of 10 equivalents of dry hydrochloric acid (acetyl chloride +methanol) for 24 hours, and 1.03 g of chemically pure laevorotatory alcohol are isolated.

Melting point: 76°-78° C.
Optical rotation: $[\alpha]_D^{20} = -29°$ (c=0.315; EtoH).
Enantiomeric excess: ee=90% (chiral HPLC).

3.2 (+)-2-{3-(5-Fluoro-2-methoxyphenyl)-1-piperazinyl]-2-hydroxypropyl}-1H-isoindole-1,3(2H)-dione.

1.03 g (0.004 mol, ee=90%) of (-)-2-(3-chloro-2-hydroxypropyl)-1H-isoindole-1,3(2H)-dione and 0.84 g (0.004 mol) of 1-(5-fluoro-2-methoxyphenyl)piperazine are dissolved in 10 ml of xylene, and the mixture is heated to reflux in the presence of a trace of sodium iodide for 12 hours.

The solvent is evaporated off and the residue is purified by chromatography on a silica gel column (eluent: cyclohexane/ethyl acetate 60:40). 0.62 g of white solid is isolated.

Melting point: 126°-130°.
Optical rotation: $[\alpha]_D^{20} = +41.5°$ (c=0.26; EtOH).

3.3. (+)-2-[{3-[4-(5-Fluoro-2-methoxyphenyl)-1-piperazinyl]-2-hydroxypropyl)amino]-4-pyrimidinecarboxamide fumarate.

3.3a. 0.62 g (0.00145 mol) of (+)-2-{3-[4-(5-fluoro-2-methoxyphenyl)-1-piperazinyl]-2hydroxypropyl}-1H-isoindole-1,3(2H)-dione is dissolved in 40 ml of ethanol containing 0.15 ml (0.003 mol) of hydrazine hydrate, and the mixture is heated to reflux for 4 hours. The mixture is evaporated to dryness and the residue is taken up with 10 ml of water and 2.5 ml of concentrated hydrochloric acid. The mixture is heated to reflux for 1.5 hours and allowed to cool, and the insoluble material is removed by filtration. The filtrate is treated with 30% aqueous sodium hydroxide solution until the pH is $\geq 8$, and the mixture is extracted with ethyl acetate; after drying of the organic phase and evaporation of the solvent, 0.41 g of yellow oil is obtained, which product is used in the next step without further purification.

3.3b. 0 241 g (0.00153 mol) of 2-chloro-4-pyrimidinecarboxamide, 0.347 g (0.0025 mol) of potassium carbonate and a crystal of sodium iodide are added to a solution of 0.41 g (0.0014 mol) of the above compound in 10 ml of N,N-dimethylformamide. The mixture is heated to 50° C. for 5 hours under argon. The solvent is evaporated off, the residue is taken up with ethyl acetate, the solution is washed with water, the organic phase is dried over magnesium sulphate and the solvent is evaporated off. 0.76 g of product is obtained in the form of an oil, which is purified by chromatography on silica gel (eluent: dichloroemthane/methanol 97:3).

0.5 g of base is obtained.

To prepare the fumarate, 0.5 g of base (0.00123 mol) is dissolved in the heated state in 20 ml of ethanol, and 0.143 g (0.00123 mol) of fumario acid dissolved in 8 ml of ethanol is added to this solution. The solution is concentrated to 90% of the initial volume, and ethyl acetate is added to the residue until precipitation occurs. The insoluble material is filtered off and taken u in the heated state in methanol in the presence of animal charcoal. After filtration, the compound recrystallises, and 0.325 g of neutral fumarate is obtained.

Melting point: 163°-167° C.
Optical rotation: $[\alpha]_D^{20} = +10.5$ (c=0.53; EtOH)

Example 4 (Compound No. 2a)

(-)-2-[(3-[4-(5-Fluoro-2-methoxyphenyl)-1-piperazinyl]-2-hydroxypropyl}amino]-4-pyrimidinecarboxamide fumarate.

4.1. (+)-2-(3-Chloro-2-hydroxypropyl)-1H-isoindole-1,3(2H)-dione.

The 1.5 g (0.00626 mol) of alcohol rich in dextrorotatory enantiomer, obtained in Example 3.1., are subjected to an acetylation by means of 3.77 g (0.0438 mol) of vinyl acetate in the presence of 3.167 g (0.0313 mol) of triethylamine and 0.8 g of lipase P in 25 ml of tetrahydrofuran for 4 days at room temperature.

After purification by chromatography on a silica gel column (eluent: hexane/ethyl acetate 70:30), 1.02 g of chemically pure dextrorotatory alcohol are finally isolated.

Optical rotation: $[\alpha]_D^{20} = +26.2°$ (c=0.31; EtOH).
Enantiomeric excess: ee=85% (chiral HPLC).

4.2. (-)-2-{3-[4-(5-Fluoro-2-methoxyphenyl)-1-piperazinyl]-2-hydroxypropyl}-1 H-isoindole-1,3(2H)-dione.

1.02 g (0.004 mol, ee=85%) of (+)-2-(3-chloro-2-hydroxypropyl)-1 H-isoindole-1,3(2H)-dione and 0.84 g (0.004 mol) of 1-(5-fluoro-2-methoxyphenyl)-piperazine are dissolved in 10 ml of xylene, and the mixture is heated to reflux in the presence of a trace of sodium iodide for 12 hours.

The solvent is evaporated off under reduced pressure and the residue is purified by chromatography on a silica gel column (eluent: dichloromethane/methanol 90:10). 1.3 g of yellow solid are obtained, which product is used in the next step without further purification.

4.3. (-)-2-[(3-[4-(5-Fluoro-2-methoxyphenyl)-1-piperazinyl]-2-hydroxypropyl}amino]-4-pyrimidinecarboxamide fumarate.

4.3a. 1.3 g of the above compound are dissolved in 40 ml of ethanol, and the mixture is heated to reflux for 1.5 hours in the presence of 0.157 g (0.003 mol) of hydrazine hydrate.

The mixture is concentrated under reduced pressure and the residue is treated with 20 ml of water and 5 ml of concentrated hydrochloric acid. The mixture is heated to reflux for 1.5 hours and cooled, the insoluble material is removed by filtration and the filtrate is treated with 30% sodium hydroxide solution until the pH is $\geq 8$. The organic phase is separated after settling has taken place and dried, and the solvent is evaporated off under reduced pressure. 0.35 g of a yellow oil is obtained, which product is used in the next step without further purification.

4.3b 0.207 g (0.00132 mol) of 2-chloro-4-pyrimidinecarboxamide, 0.273 g (0.0021 mol) of potassium carbonate and a crystal of sodium iodide are added to a solution of 0.35 g (0.0012 mol) of the compound obtained above in 20 ml of N,N-dimethylformamide. The mixture is heated to 50° C. for 5 hours under argon. The solvent is evaporated off under reduced pressure and an oil is obtained, which oil is purified by chromatography on a silica gel column (eluent: dichloromethane/methanol 97:3). 0.290 g of base is isolated, the fumarate of which is prepared by dissolving it in 10 ml of ethanol in the heated state and adding 0.083 g (0.00072 mol) of fumaric acid dissolved in 4 ml of ethanol. The solution is concentrated under reduced pressure to 90% of its initial volume, and ethyl acetate is added to the residue until precipitation occurs. The solid is filtered off and dried.

Melting point: 161°-163° C.

Optical rotation: $[\alpha]_D^{20} = -8.25°$ (c=0.57; EtOH).

Example 5 (Compound No. 7)

(±)-2-[{3-[4-(5-Chloro-2-methoxyphenyl)-1-piperazinyl]-2-methoxypropyl}amino]-4-pyrimidinecarboxamide.

5.1 (±)-α-(Triphenylemthylaminomethyl)-4-(5-chloro-2-methoxyphenyl)-1-piperazineethanol.

3 ml, equivalent to 2.175 g (0.0215 mol), of triethylamine are added to a solution of 5.89 g of (±)-α-(aminomethyl)-4-(5-chloro-2-methoxyphenyl)-1-piperazineethanol (purity 90%, equivalent to 0.020 mol) in 150 ml of dichloromethane. The mixture is cooled to 0° C., and a solution of 5.45 g (0.0195 mol) of triphenylmethyl chloride dissolved in 150 ml of dichloromethane is added in the space of 6 hours. The mixture is left stirring for 2 hours and then left standing overnight. It is treated with aqueous sodium hydrogen carbonate solution, the organic phase is separated after settling has taken place, washed with water and dried over magnesium sulphate, and the solvent is evaporated off. The residue is treated with acetonitrile, and the product crystallises in the cold state.

8.55 g of beige solid are obtained.

Melting point: 170.5°-172.5° C.

5 2. (±)-3-[4-(5-Chloro-2-methoxyphenyl)-1-piperazinyl]-2-methoxypropanamine.

5.2a. 3 g (0.0055 mol) of (±)-α-(triphenylmethylaminomethyl)-4-(5-chloro-2-methoxyphenyl)-1-piperazineethanol, 1 ml of N,N-dimethylformamide and 3.42 g (0.0241 mol) of methyl iodide are added to a suspension of 1 g of 60–65% sodium hydride suspension in oil (0.025–0.027 mol), washed beforehand with pentane, in 25 ml of tetrahydrofuran. The mixture is heated to 45°-50° C. for 4 hours, then cooled and treated with methanol added dropwise. The solvents are evaporated off under reduced pressure and the residue is purified by chromatography on a silica gel column (eluent: cyclohexane, then cyclohexane/-dichloromethane 50:50).

1.5 g of compound are isolated, which product is used in the next step without further purification.

5.2b. A stream of dry gaseous hydrochloric acid is passed for 10 minutes into a solution of 2.9 g (0.052 mol) of the compound obtained above in 80 ml of methanol. The mixture is left stirring for 0.5 hour and the solvent is then evaporated off under reduced pressure. The residue is treated with water and dichloromethane and with 30% sodium hydroxide solution, the organic phase is separated and dried over magnesium sulphate, the solvent is evaporated off under reduced pressure and 1.7 g of solid are obtained, which product is used in the next step without further purification.

5.3. (±)-2-[{3-[4-(5-Chloro-2-methoxyphenyl)-1-piperazinyl]-2-methoxypropyl}amino]-4-pyrimidinecarboxamide.

1.65 g (0.0052 mol) of compound obtained above, 0.81 g (0.0051 mol) of 2-chloro-4-pyrimidinecarboxamide and 0.85 g (0.0061 mol) of potassium carbonate are introduced successively into 70 ml of acetonitrile, and the mixture is heated to reflux for 7 hours.

The mixture is allowed to cool and is then concentrated to dryness. The residue is treated with water and dichloromethane, the organic phase is separated and dried and the solvent is evaporated off under reduced pressure. The residue is purified by chromatography on a silica gel column (eluents: dichloromethane, then dichloromethane/ethyl acetate 50:50, then dichloromethane/methanol 99:1, then 90:10). 0.81 g of yellowish solid is isolated.

Melting point: 152.5°-154° C.

The table which follows illustrates the chemical structures and physical properties of a few compounds of the invention.

TABLE

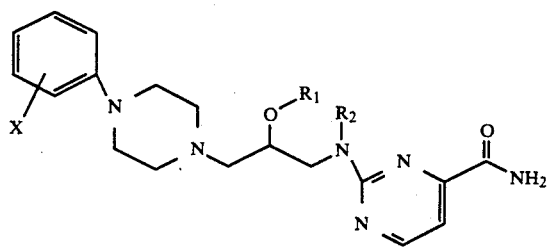

(I)

| N° | X | R₁ | R₂ | Salt | M.p. (°C.) |
|---|---|---|---|---|---|
| 1 | 3-Cl | H | H | HCl | 249–250 |
| 2 | 5-F, 2-OCH₃ | H | H | ½ fum | 199.5–202.5 |
| 2a | $[\alpha]_D^{25} = -8\ 25°$ (c = 0.57; H₂O) | | | fum | 161–163 |
| 2b | $[\alpha]_D^{25} = +10\ 5°$ (c = 0.53; H₂O) | | | ½ fum | 163–167 |
| 3 | 5-Cl, 2-OCH₃ | H | H | HCl | 231–235 (dcp) |
| 4 | 2-cC₃H₅ | H | H | HCl | 253–254 |
| 5 | 5-Cl, 2-OCH₃ | H | CH₃ | HCl | 231–235 (dcp) |
| 6 | 2-cC₃H₅ | H | CH₃ | HCl | 194–198 |
| 7 | 5-Cl, 2-OCH₃ | CH₃ | H | — | 152.5–154 |
| 8 | 5-Cl, 2-OCH₃ | nC₃H₇ | H | — | 147–148 |

Legend

The compounds 2a and 2b are the laevorotatory and dextrorotatory enantiomers, respectively, of the compound 2, in the "X" column, "cC₃H₅" denotes a cyclopropyl group; in the "R₁" column, "nC₃H₇" denotes a propyl group; in the "Salt" column, "HCl" denotes a hydrochloride, "fum" denotes an acid fumarate, "½ fum" denotes a neutral fumarate and "—" denotes a compound in the state of a base; in the "M.p(° C.)" column, "(dcp)" denotes a melting point with decomposition.

The compounds of the invention were subjected to studies of their antagonist activity with respect to α₁-adrenoceptors in the lower urinary tract.

Their in vitro activity was studied on isolated rabbit urethra.

Rings of adult rabbit urethra are prepared according to the method of Ueda et al., Eur. J. Pharmacol., (1984), 103, 249–254, and then, after sensitisation to noradrenaline, the curve of concentration-response to phenylephrine is determined in the absence and presence of the test compound.

The potency of the $\alpha_1$-adrenergic antagonism of each compound is evaluated by calculating the pA$_2$, the antilogarithm of the molar concentration of antagonist in the presence of which the agonist concentration must be doubled in order to generate the same effect as in its absence.

The pA$_2$ values of the compounds are of the order of 5.5 to 9.

The in vivo activity of the compounds of the invention was studied in respect of their effect on urethral hypertonia generated by stimulation of the sympathetic fibres of the hypogastric nerve in anaesthetised cats.

Adult male cats were anaethetised with pentobarbitone sodium, and prepared according to the method of Theobald, J. Auton. Pharmac., (1983), 3, 235–239, so as to obtain a urethral hypertonia by stimulation of the sympathetic fibres of the hypogastric nerve. The contractile responses of the urethra to electrical stimulation of the hypogastric nerve are noted before and after intravenous administration of the test compounds at cumulative doses from 1 to 1,000 μg/kg.

The potency of the $\alpha_1$-adrenergic antagonism of each compound is evaluated by calculating the ID$_{50}$, the dose which inhibits urethral hypertonia by 50%.

The ID$_{50}$ values of the compounds of the invention are of the order of 0.01 to 1 mg/kg.

The results of the tests show that the compounds of the invention show in vitro an antagonist activity with respect to the $\alpha_1$-adrenoceptors of the smooth muscles of the lower urinary tract (urethra) when the muscles are stimulated by an $\alpha_1$-adrenergic agonist (phenylephrine). In vivo, they inhibit urethral hypertonia generated by sympathetic nerve stimulation.

The compounds of the invention can hence be used for the symptomatic treatment of diseases and complaints involving a hyperactivity of the $\alpha_1$-adrenergic system in the lower urinary tract, and in particular for the treatment of benign hypertrophy of the prostate, dysuria and pollakiuria. They may thus be formulated as pharmaceutical compositions in which they are the active ingredient.

For this purpose, they may be presented in all forms suited to enteral or parenteral administration, in combination with pharmaceutical excipients, for example in the form of tablets, dragees, capsules including hard gelatin capsules, solutions or suspensions to be taken by mouth or injected, and suppositories, their content being such as to permit a daily dose of 0 5 to 500 mg of active substance.

We claim:

1. A compound which is a 4-pyrimidinecarboxamide derivative of formula (I)

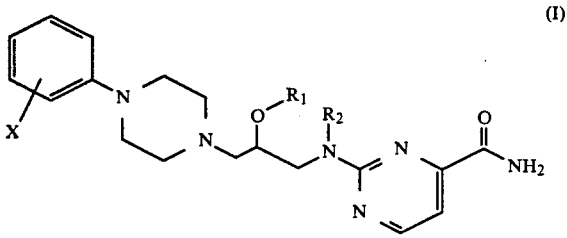

in which

X represents one or more substituents independently selected from the group consisting of fluorine, chlorine, methoxy and cyclopropyl, R$_1$ represents a hydrogen atom or a C$_1$-C$_3$ alkyl group, and R$_2$ represents a hydrogen atom or a methyl group a or a pharmaceutically acceptable acid additional salt thereof.

2. A compound according to claim 1, in the form of a pure enantiomer or a mixture of enantiomers.

3. A compound according to claim 1, in which X represents one or two substituents independently selected from the group consisting of fluorine, chlorine, methoxy and cyclopropyl and R$_1$ represents hydrogen, methyl or n-propyl.

4. A compound according to claim 1, in which the pharmaceutically acceptable acid addition salt is the hydrochloride, acid fumarate or neutral fumarate.

5. A compound according to claim 1, which is:

($\pm$)-2-[{3-[4-(5-chloro-2-phenoxyphenyl)-1-piperazinyl]-2hydroxypropyl}amino]-4-pyrimidinecarboxamide or the hydrochloride thereof;

($\pm$)-2-[{3-[4-(5-chloro-2-methoxyphenyl)-1-piperazinyl]-2hydroxypropyl}methylamino]-4-pyrimidinecarboxamide or the hydrochloride thereof;

(+)-2-[{3-[4-(5-fluoro-2-methoxyphenyl)-1-piperazinyl]-2hydroxypropyl}amino]-4-pyrimidinecarboxamide or the neutral fumarate thereof;

(−)-2-[{3-[4-(5-fluoro-2-methoxyphenyl)-1-piperazinyl]-2hydroxypropyl}amino]-4-pyrimidinecarboxamide or the acid fumarate thereof; or ($\pm$)-2-[(3-[4-(5-chloro-2-methoxyphenyl)-1-piperazinyl]-2methoxypropyl}amino]-4-pyrimidinecarboxamide.

6. A pharmaceutical composition comprising a pharmaceutically acceptable carrier and, as an active ingredient, a compound as claimed in claim 1.

7. A process for preparing a compound according to claim 1, which process comprises:

reacting a piperazine of formula (II)

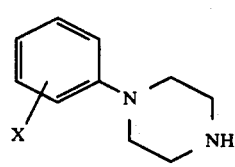

with an epoxide of formula (III) or an alcohol of formula (III'),

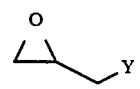

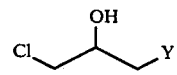

in which Y represents a phthalimido group, to obtain a derivative of formula (IVa); and then

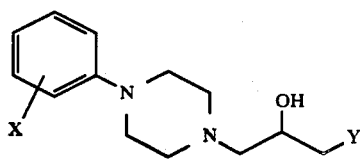
(IVa)

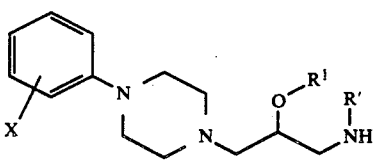
(V)

a) when $R_1$ and $R_2$ each represent hydrogen, treating the derivative of formula (IVa) with hydrazine hydrate and then with aqueous hydrochloric acid to obtain the hydrochloride of an amine of formula (V),

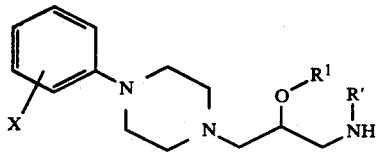
(V)

in which $R_1$ and $R'$ each represent hydrogen, which amine is then reacted with 2-chloro-4-pyrimidinecarboxamide to obtain a compound of formula (I) in which $R_1$ and $R_2$ are each hydrogen; or b) when $R_1$ represents a $C_1$-$C_3$ alkyl group, converting the compound of formula (IVa) into a compound of formula (IVb),

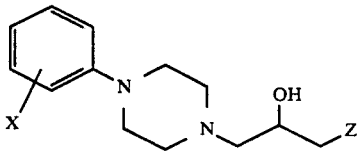
(IVb)

in which Z represents a triphenylmethyl group, by deprotecting the compound of formula (IVa) using hydrazine hydrate, and then by protecting the amine thereby liberated using triphenylmethyl chloride, to obtain the compound of formula (IVb) which is then reacted with a $C_1$-$C_3$ alkyl halide in the presence of a base, the amine function of the compound thereby obtained is then deprotected by means of gaseous hydrochloric acid in a protic solvent to obtain the hydrochloride of an amine of formula (V)

in which $R_1$ represents a $C_1$-$C_3$ alkyl group and $R'$ represents a hydrogen atom, which is then reacted with 2-chloro-4-pyrimidinecarboxamide to obtain a compound of formula (I) in which $R_1$ represents a $C_1$-$C_3$ alkyl group; or c) when $R_2$ represents a methyl group, reacting a compound of formula (V) obtained as in step a) or b) with an alkyl formate, to obtain a compound of formula (V) in which $R'$ represents a formyl group, which is reduced in the presence of lithium aluminum hydride and then reacted with 2-chloro-4-pyrimidinecarboxamide to obtain a compound of formula (I) in which $R_2$ represents a methyl group, the substituent X being as defined in claim 1.

8. A process according to claim 7, in which the reaction of the piperazine of formula (II) with the epoxide of formula (III) takes place in an aliphatic alcohol at a temperature of from 20° to 100° C.

9. A process according to claim 7, in which the reaction of the compound of formula (V) with 2-chloro-4-pyrimidinecarboxamide takes place in an aprotic solvent in the presence of a bases at a temperature of from 20° to 60° C.

10. A process according to claim 9, in which the aprotic solvent is N,N-dimethylformamide.

11. A process according to claim 9 in which the base is potassium carbonate.

12. A process according to claim 7, further comprising the step of converting the compound of formula (I) obtained from step a), b) or c) into a pharmaceutically acceptable acid addition salt.

13. A process according to claim 7, in which the reaction of the piperazine of formula (II) with the alcohol of formula (III') takes place in xylene at the refluxing temperature of xylene.

14. A method of treating a disease or complaint involving hyperactivity of the $\alpha_1$-adrenergic system which comprises administering to a patient an effective amount of a compound as claimed in claim 1.

* * * * *